(12) United States Patent
Engstad et al.

(10) Patent No.: US 9,750,688 B2
(45) Date of Patent: *Sep. 5, 2017

(54) GLUCAN GELS

(71) Applicant: BIOTEC PHARMACON ASA, Tromsø (NO)

(72) Inventors: Rolf Engstad, Tromsø (NO); Stein-Tore Solem, Tromsø (NO); Dag-Eirik Ramsøy, Tromsø (NO)

(73) Assignee: BIOTEC PHARMACON ASA, Tromsø (NO)

( * ) Notice: Subject to any disclaimer, the term of this patent is extended or adjusted under 35 U.S.C. 154(b) by 0 days.

This patent is subject to a terminal disclaimer.

(21) Appl. No.: 15/066,748

(22) Filed: Mar. 10, 2016

(65) Prior Publication Data

US 2016/0256385 A1 Sep. 8, 2016

Related U.S. Application Data

(62) Division of application No. 13/989,594, filed as application No. PCT/GB2011/052358 on Nov. 29, 2011, now Pat. No. 9,314,432.

(30) Foreign Application Priority Data

Nov. 29, 2010 (GB) .................................. 1020191.1

(51) Int. Cl.
| | | |
|---|---|---|
| A61K 9/06 | (2006.01) | |
| C08B 37/00 | (2006.01) | |
| C08J 3/075 | (2006.01) | |
| A61K 31/716 | (2006.01) | |
| A61L 15/00 | (2006.01) | |
| A61L 26/00 | (2006.01) | |
| A61K 9/00 | (2006.01) | |

(52) U.S. Cl.
CPC .............. *A61K 9/06* (2013.01); *A61K 9/0014* (2013.01); *A61K 31/716* (2013.01); *A61L 15/00* (2013.01); *A61L 26/0023* (2013.01); *C08B 37/0024* (2013.01); *C08J 3/075* (2013.01); *C08J 2305/00* (2013.01)

(58) Field of Classification Search
CPC ... C08B 37/0024; C08J 3/075; C08J 2305/00; A61K 9/06; A61K 9/0014; A61K 31/716; A61L 15/00; A61L 26/0023
See application file for complete search history.

(56) References Cited

U.S. PATENT DOCUMENTS

| | | | |
|---|---|---|---|
| 5,158,772 A | 10/1992 | Davis | |
| 5,322,841 A | 6/1994 | Jamas et al. | |
| 6,242,594 B1 | 6/2001 | Kelly | |
| 6,875,754 B1 | 4/2005 | Griesbach et al. | |
| 2004/0023923 A1 | 2/2004 | Morgan | |
| 2009/0004201 A1 | 1/2009 | Engstad | |
| 2010/0322923 A1 | 12/2010 | Seljelid et al. | |
| 2011/0008476 A1 | 1/2011 | Johansen et al. | |

FOREIGN PATENT DOCUMENTS

| | | |
|---|---|---|
| WO | 95/30022 A1 | 11/1995 |
| WO | 9530022 A1 | 11/1995 |
| WO | 9628476 A1 | 9/1996 |
| WO | 99/21531 A1 | 5/1999 |
| WO | 02058711 A1 | 8/2002 |
| WO | 2004/039378 A1 | 5/2004 |
| WO | 2009063221 A2 | 5/2009 |

OTHER PUBLICATIONS

Pu Qinglin, "Research on Interaction of Yeast Glucan With Other Macromolecular Substances", China Excellent Doctoral and Master's Theses (Master) Engineering Science and Technology vol. I, Issue 2, Feb. 15, 2007, with English-language translation (94 pages with translation).

Matsuda, Kazuo (Jul. 1, 1999) "Separation and Purification Method of Polysaccharides" Seibutukagaku Jikkenhou, vol. 20, pp. 23-28, Center for Academic Publications Japan, Co. Ltd., Jul. 1, 1999, with English-language translation.

Sletmoen, Marit, et al., "Review Higher Order Structure of (1,3)-β-D-Glucans and Its Influence on Their Biological Activities and Complexation Abilities," Biopolymers, vol. 89, No. 4, pp. 310-321 (2008).

Steiner, E., et al., "Rheological properties of solutions of a colloid-disperse homoglucan from Schizophyllum commune," Progress in Colloid & Polymer Science, vol. 77, pp. 217-220 (1988).

Xu, Jingyuan, et al., "Micro-heterogeneity and micro-rheological properties of high-viscosity oat β-glucan solutions," Food Chemistry, vol. 103, pp. 1192-1198 (2007).

*Primary Examiner* — Suzanne Ziska

(74) *Attorney, Agent, or Firm* — Rothwell, Figg, Ernst & Manbeck, P.C.

(57) ABSTRACT

The present invention relates to a glucan having a weight average molar mass of 15,000 to 50,000 g/mol on a single chain basis and a weight average molar mass in aqueous solution on an aggregate basis of 4 to $20 \times 10^5$ g/mol and existing in gel form in aqueous solution at a concentration ≥1% at 25° C. and neutral pH and having a melting temperature (gel to sol) of 35 to 60° C. when the glucan is dissolved in water at a concentration of 2%, methods for the production thereof, medical uses thereof, physical supports having the glucan applied thereto or impregnated thereon and in vitro methods of proliferation of skin cells which comprise contacting a population of skin cells with the glucan.

13 Claims, 12 Drawing Sheets

GLUCAN GELS

This application is a division of U.S. patent application Ser. No. 13/989,594 filed 9 Aug. 2013, which in turn is a filing under 35 USC 371 of International Application No. PCT/GB2011/052358, filed 29 Nov. 2011, which claims priority to GB Application No. 1020191.1, filed 29 Nov. 2010. Each application is incorporated herein by reference.

The present invention relates to a new glucan product, to processes for its manufacture and to uses thereof as a pharmaceutical, incorporated in a medical device, as a nutraceutical, cosmetic product or the like.

Glucans are a heterogeneous group of glucose polymers found in the cell walls of plants, bacteria, fungi and protozoa. Glucans have a backbone chain and in some cases side chains which, depending of the origin of the glucan, comprise $\beta(1,3)$, $\beta(1,4)$ and/or $\beta(1,6)$-linked glucosyl units. Depending upon the source and method of isolation, beta-glucans have various degrees of branching and type of linkage in the backbone and side chains. The frequency and type of linkage in the side chains is highly relevant to the molecule's biological activity. Glucans also differ highly in their molecular weight as well as in their tendency for chain aggregation which both are essential features for the efficacy profile of these molecules. Most beta-glucans of fungal and yeast origin are in their native state insoluble in water, but can be made soluble either by acid hydrolysis or by derivatization introducing foreign groups like -phosphate, -sulphate, -amine, -carboxymethyl and so forth to the molecule.

In Europe, Asia and USA, beta-glucans especially from Bakers' yeast have long been employed as feed additives for animals, in cosmetics, as dietary supplement for humans, as immunomodulators e.g. in treatment of wounds, and as an active ingredient in skin cream formulations. Glucans have been employed in the treatment of cancer as shown in WO02/058711. Beta-glucans are, in this context, regarded as immunostimulants increasing the activity of white blood cells partly by inducing well regulated and site restricted inflammatory reaction localised to the cancer. Their use in the treatment of inflammatory bowel disease has also been described in WO 2009/063221. Further applications of glucans within wound treatment are described in EP 815144 and in U.S. Pat. No. 6,875,754 as well as for the treatment of asthma and allergy as described in U.S. Ser. No. 12/528, 215.

Cereal glucans comprise generally unbranched chains of $\beta(1,3)$ and a significant share of $\beta(1,4)$ linkages, while yeast glucans are made up of predominantly $\beta(1,3)$ linked glucosyl residues with $\beta(1,6)$ linkages acting as branch points for side chains which may comprise both $\beta(1,3)$ and $\beta(1,6)$ linked glucosyl residues. Other molecules classed as glucans include curdlan, a basically linear molecule made up of $\beta(1,3)$ linked glucosyl residues without branches. Lentinan is a glucan with a $\beta(1,3)$ linked backbone but incorporating single $\beta(1,6)$ linked glucosyl residues attached essentially regularly to the backbone giving a haircomb structure of this molecule. The single $\beta(1,6)$ linked glucosyl residues attached to the backbone equivalent to a $\beta(1,3,6)$ linkage point but no further molecules are attached to this linkage point and thus glucans like lentinan do not have side chains. Other examples of this group of glucans are scleroglucan, laminarin and schizophyllan.

Variations in branching and the length and structure of the side chains lead to contrasting secondary and tertiary structures and thus biological activities. The higher order structures of glucans vary considerably and molecular weight, solubility and particle size will all influence activity in a generally unpredictable manner. Some products are extremely potent inducers of inflammatory cytokines in target cells, whereas others have the opposite effect, completely inhibiting cytokine release. Typical for many insoluble beta-glucan products is the induction of a whole range of inflammatory responses, where e.g. injection of insoluble beta-glucan formulations has been associated with granuloma formation, arthritis induction and increased susceptibility against gram negative sepsis. On the other side, soluble beta-glucans are not reported to be encumbered with such negative side effects, but their efficacy as immunostimulants have been known to vary substantially.

It has been shown (WO 95/30022), for example, that a glucan product derived from yeast which has been modified by glucanase treatment to selectively remove (1,6) linked side chains is more potent in stimulating the immune system of fish than a product with intact (1,6) linked side chains.

Glucans have great potential as therapeutic agents and adjuvants but the vast range of structural variability, problems of analysis with such large and complex molecules and the lack of understanding about mechanism of action and receptors for these molecules, means that there is still a great need for an improved glucan product with tailor-made biological activities, and for controllable and repeatable processes for manufacture of homogeneous products.

Beta-glucans are known to be so-called Pathogen Associated Molecular Patterns as they are found at the surface of a number of pathogenic (micro)organisms, especially fungi. Higher organisms have thus evolved mechanisms for recognizing these types of structures in order to find and destroy intruders belonging to this class of organism. In mammals the so called innate immune cells express specific receptors recognizing beta-glucans, and one of the most prominent receptors is called Dectin-1. Other receptors are also involved in the recognition or signal transduction induced by beta-glucans, amongst these are CD11b/CD18 (CR3), and toll receptors 2 and 4 (TLR2 and TLR4). Of the cells involved in recognizing beta-glucans are the typical phagocytes of the innate immune system, i.e. monocyte, macrophages, dendritic cells, and granulocytes, but also Natural Killer cells as well as a number of endothelial cells and other more tissue specific cells have the ability to express beta-glucan receptors.

The crucial step in inducing a biological response in the target cells is the initial binding to the receptor and furthermore, it seems, the ability of the beta-glucan formulation to cross-link a sufficient number of receptors in order to induce an adequate signal-transduction into the cell. The present invention describes a product and a method for making a product that has the ability to cross-bind receptors inducing a specific type of biological activity. This is in contrast to insoluble products that could induce a massive response by cross-binding a large number of receptors and secondly be phagocytosed, which due to the nature of the insoluble (or "crystalline like") glucan leads to lysosomal rupture within the cell inducing NLRP inflammasome activation. Insoluble beta-glucans may also induce ROS (reactive oxygen species) that also would trigger inflammasome activation leading to an unfavorable inflammatory reaction. The current invention describes beta-glucans products that are able to induce a significant inflammatory response that would activate several immune mechanisms, but without triggering inflammasome activation that is typical for a number of (aggregated insoluble) beta-glucan products.

The present invention potentiates glucan efficacy by establishing a pharmaceutically beneficial supramolecular structure in the final product.

The importance of higher order structure amongst β-glucans and the contribution of the character of both individual glucan strands or chains and the higher order structure to the overall activity of the glucan product is described by Sletmoen et al. in Biopolymers vol. 89, No. 4 pp 310-321, 2008. Higher order structure may comprise a regular arrangement such as a triple helix or a more loose aggregation.

The present invention provides a glucan formulation that is perceived as a moderately sized entity when encountered by the target cells, but when phagocytosed the glucan is easily taken up into phagosomes without inducing lysosomal rupture. The present invention thus describes a novel organization of a highly potent soluble beta-glucan with good gelling properties. Without wishing to be bound by theory it seems that the glucan molecules are arranged in a type of higher complex and loose "haystack" arrangement kept together by relatively weak hydrogen bonds between the frequent —OH groups along the glucan backbone structure. The "haystack" organization has the potential of presenting a number of sites on its surface available for recognition by specific glucan receptors on the target cells. The "haystack" organized molecules do not, however, harbor the rigidity of an insoluble product, but would much more easily become "degraded" and thus "immobilized" at the site or after phagocytosis. Such a large higher order organization is advantageous as compared both to insoluble and to known soluble products, since it gives an immunomodulatory response mimicking many of the effects observed with particulate and insoluble beta-glucans without inducing less controllable and possible harmful effects known to be associated with insoluble beta-glucans.

In one aspect the present invention provides a glucan having a weight average molar mass on a single chain basis of 15,000 to 50,000 g/mol and a weight average molar mass in aqueous solution on an aggregate basis of 4 to $20 \times 10^5$ g/mol, said glucan existing in gel form when dissolved in water at a concentration $\geq 1\%$ at 25° C. and neutral pH and having a melting temperature (gel to sol) above 30° C., preferably between 35° C. and 80° C., more preferably between 35 and 60° C., still more preferably between 37° C. and 60° C., most preferably about 40° C. when the glucan is dissolved in water at a concentration of 2%.

Preferably the glucan is in aqueous solution at a concentration of 1.5 to 6%, more preferably 1.5 to 5%, still more preferably 2 to 4%, most preferably about 2%. It is understood that a "gel" form can be considered an aqueous solution.

In a preferred aspect the glucan is a beta glucan, preferably it has a backbone of β(1,3) linked glucosyl residues and side chains of β(1,3) linked glucosyl residues (e.g. side chains of at least 2, 5, 10 or 20 linked glucosyl residues) attached thereto via a β(1,6) linkage.

"Neutral pH" means pH 7.

A "single chain" refers to an individual glucan molecule, i.e. one in which the glycosyl residues are covalently linked. "Aggregates" form through hydrogen bond interactions and define a supramolecular or higher order structure. Such associations are less permanent than provided by covalent bonding but the methods described herein result in recognisable patterns of aggregation, whose average molar mass can be analysed using the techniques referred to herein. The "aqueous solution" is typically pH 7.

Alternatively viewed, the present invention provides a gel glucan product comprising glucan in aqueous solution at a concentration of 1 to 6%, the glucan having a weight average molar mass on an aggregate basis of 4 to $20 \times 10^5$ g/mol and a weight average molar mass on a single chain basis of 15,000 to 50,000 g/mol, the gel glucan product having a melting temperature (gel to sol) above 30° C., preferably between 35° C. and 80° C., more preferably between 35 and 60° C., still more preferably between 37° C. and 60° C., most preferably about 40° C.

Glucan products are usually particulate or in some cases soluble. Gel forms are very unusual, but the present gel product has been found to provide excellent biological activity, in particular in wound healing, as compared to other glucan products. In wound healing it is of utmost importance to apply a pharmaceutical or medical device in a manner which secures the moisturization of the wound and the products must cover and stick to the wound surface to avoid infections and provide for an administration profile as deemed relevant by a medical practitioner or necessary due to the type of wound. Usually, glucans in their particulate, semi-soluble or liquid form do not solve these basic requirements either because they are not effective, they are in a state which is not applicable for wound healing purposes, or both. The glucan of the present invention combines these necessary characteristics thus making it useful for all applications where a pure glucan gel may find a proper use. In addition to strictly topical applications, other possible uses could be oral and/or mucosal administration, such as treating diseases of the gastro-intestinal tract or the oral cavity in addition to cancer therapy for which the present gel product has been found to have excellent activity. The excellent adhesion properties of the glucan according to the present invention enable it to cover the mucosal lining at the site of action and thus accelerate the healing process. Thus the glucans of the invention have particular utility in the treatment of oral mucositis and other indications affecting the mucosa.

According to the present invention a novel organization of a soluble glucan into a gel structure can be obtained by treating an adequately concentrated solution of soluble glucan with an agent able to dissociate hydrogen bonds both between and within glucan chains, followed by adding an agent rapidly able to restore inter- and intra-chain hydrogen bonding interactions. The supramolecular tertiary, or 3-dimensional, structure of a glucan, in this case the arrangement of the molecular chains within the glucan product as a whole, appears to be of utmost importance for efficacy. Without wishing to be bound by theory it seems that only biologically effective molecular structures provide for binding to different receptors at the target cells. Single chain, short chain or products not structured in an appropriate 3-dimensional complex manner will not be able to stimulate the body's immune system in the same way.

There are limited ways to characterize the 3-dimensional (also defined as tertiary or supramolecular structure) molecular structure of a gel comprised by its single chains. General ways of describing such a gel can be by the average molar mass and molar mass distribution of the single chains, as well as by physical characteristics such as viscosity. In the case of immunomodulating products, gels can also be indirectly described by their biological efficacy profile, or in other words measuring of the so-called "biological fingerprint". When using molecular mass as a defining physical characteristic, it is recognised that the analysis methods are generally destructive, leading to the analysis of the single chain components of the gel product, or smaller aggregated structures, rather than giving a detailed picture of the molecular interactions between these single chains which are necessary to give a biologically effective 3-dimensional supramolecular structure. Nevertheless a detailed analysis of several other physical characteristics of glucans including their viscosity combined with a biological efficacy profile will enable the skilled man to distinguish between a variety of different glucans. One of these criteria is a specific molecular mass range.

The molar mass of glucans can be determined in different ways. In the case of a soluble glucan product the molar mass is conveniently measured by SEC-MALS-RI (size exclusion chromatography with multi-angle light scattering and refractive index detection) analysis, and such analysis provides a weight average molar mass value ($M_w$) for the sample as well as the distribution of different molecular weights within the sample. In the present invention, the weight average molecular mass ($M_w$) is defined as follows:

$$M_w = \frac{\Sigma n_i M_i^2}{\Sigma n_i M_i} = \frac{\Sigma c_i M_i}{\Sigma c_i}$$

where $n_i$ is the number of molecules with molar mass $M_i$. The weight concentration $c_i$ of molecules with molar mass $M_i$ is proportional to the molar mass $M_i$ and the number of molecules $n_i$:

$$c_i = M_i n_i \rightarrow n_i = c_i / M_i$$

The weight concentration for each slice of the chromatogram is measured by the RI-detector while the molar mass for each slice in the chromatogram is measured by the MALS-detector in combination with the RI-detector. The calculations are based on light scattering theory.

Specifically, the average molar mass (for single chains) according to the present invention is determined by SEC-MALS-RI in DMAc with 0.5% LiCl (dimethylacetamide with 0.5% lithium chloride) assuming a dn/dc of 0.12 for the glucan in this solvent. The DMAc/LiCl solvent fully dissolves the said glucan into single chains, and subsequent SEC-MALS-RI analysis with DMAc with 0.5% LiCl as eluent therefore gives a measure of the molecular weight distribution on a single chain level. In short, the analysis of the glucan in DMAc/LiCl involves dissolution of the dry glucan in the solvent at a concentration of approximately 3 mg/ml by stirring the solution at r.t. over night and heating it at 100° C. for 1 h, prior to the analysis by SEC-MALS-RI using 3×PLgel Mixed-A LS columns and DMAc with 0.5% LiCl as eluent. The weight average molar mass for the glucan of the present invention on a single chain basis determined by this method is 15,000 to 50,000 g/mol, preferably 25,000 to 45,000 g/mol, and more preferably 30,000 to 40,000 g/mol.

In aqueous solution the weight average molar mass of the mainly higher order structures and aggregates present is 4-20×10$^5$ g/mol, preferably 5-15×10$^5$ g/mol, and more preferably 6-12×10$^5$ g/mol. These averages are preferably calculated when very large aggregates, i.e. molar mass above 1.0×10$^7$ g/mol, are excluded. The analysis of the glucan in aqueous solution involves diluting the gel solution to approximately 3 mg/ml in 0.1 M NaNO$_3$ with 0.02% NaN$_3$, heating to 100° C. in a capped glass tube for 30 min, cooling to room temperature, filtrating through a 0.2 μm syringe filter, and analysis by SEC-MALS-RI using TSKgel G5000 PWXL+TSKgel G4000 PWXL columns and 0.1 M NaNO$_3$ with 0.02% NaN$_3$ as eluent. Similar set-ups with for example 0.05 M Na2SO4/0.01 M EDTA as solvent/eluent gives equivalent results. The combination of molar mass values for the single chains and the higher order structures/aggregates in aqueous solution gives a good indication of the molecular and supramolecular structure of the gel as a whole and usefully defines the glucans of the present invention.

The glucans of the present invention are further characterized by being in gel form at 25° C. and at a pH between 3 and 8. The glucan gels of the invention are further characterised by their viscosity profile exemplified by the melting temperature of the gels (gel to sol) of above 30° C. and up to approximately 80° C., preferably above normal body temperature, more preferably between 37° C. and 60° C., most preferably between 39° C. and 60° C., e.g. 40-50° C. The figures above are given for a glucan gel in a concentration of 2% in an aqueous solution.

The gel melting point for a glucan product, i.e. the gel→sol transition temperature, is conveniently determined by small strain oscillatory measurements using a Stresstech HR rheometer or similar and examining the viscoelastic changes during cooling (70→10° C.) and heating (10→70° C.) of the glucan solution. An example of storage modulus (G') plotted against temperature in such an experiment is shown in FIG. 1. The melting temperature for this particular sample is equivalent to where the storage modulus of the curve for increasing temperature levels out (at approx. 0 Pa), which is approx. 40° C. Another way of determining approximate melting temperature of the gel is to measure the viscosity (e.g. using a rotational viscometer) of the gel at sequentially higher temperature until the viscosity is essentially gone and the gel has transformed into a solution. The gel melting temperature is preferably 30-80° C., preferably over body temperature to guarantee a stabilized glucan gel for topical applications. Topical administration demands a comparably lower melting temperature than oral administration or administration to a site of an infection.

The glucan gel of the present invention is an aqueous gel and while the gel form can be confirmed by visual inspection, the viscosity and the pseudoplastic and thixotropic nature of the glucan gel may also be determined by viscosity measurement e.g. by using a rotational viscometer. A 2% glucan gel according to the present invention has a viscosity of at least 1000 cP, preferably at least 1500 cP, measured at 25° C. and a rotational speed of 10 rpm using a Brookfield DV-II+ Pro Programmable viscometer with a small sample adapter and spindle SC4-31 (corresponding to a shear rate of 3.40 sec$^{-1}$). A convenient method for measuring the viscosity of this pseudoplastic and thixotropic gel is to use a so called up-down rate ramp, for example starting at 2 rpm and going up in 2 rpm increments to 10 rpm and then going back down again in 2 rpm steps. The data from such an experiment can both demonstrate the pseudoplastic (decreasing viscosity with increasing shear rate) and thixotropic (decreasing viscosity over time while subjected to shear) characteristics of the gel as well as provide a measure of e.g. 10 rpm viscosity.

The glucans of the present invention are typically derived from yeast, preferably from *Saccharomyces cerevisiae*. The basic molecular structure of these glucans is typically a β-1,3-backbone (meaning a chain of glucose molecules linked by β-1,3 linkages), in addition to β-1,3 side chains (meaning a chain of at least two glucose molecules linked by β-1,3 linkages) and a β-1,3,6-linkage point linking the side chains to the backbone. In addition, glucans from yeast comprise β-1,6 linkages which may be linked to the side chains or directly to the backbone. Further types of linkages do exist but at a comparably low level. Other yeasts which may provide a source for the glucan include Brewers yeast, *Candida* sp. like *Candida albicans*, *Candida cloacae*, *Candida tropicalis*, *Candida utilis*, *Hansenula* sp. like *Hansenula wingei*, *Hansenula arni*, *Hansenula henricii* and *Hansenula americana*, *Histoplasma* sp., *Kloeckera* sp., *Kluyveromyces* sp. like *Kluyveromyces lactis*, *Kluyveromy-* ces *fragilis, Kluyveromyces polysporus, Pichia* sp., *Rhodotorula* sp., *Saccharomyces* sp. like *Saccharomyces delbruekii, Saccharomyces rosei, Saccharomyces microellipsodes, Saccharomyces carlsbergensis* or different *Saccharomyces* strains like *Saccharomyces cerevisiae* R4 (NRRL Y-15903) and R4 Ad (ATCC No. 74181), *Schizophyllum* sp., *Schizosaccharomyces* sp. like *Schizosaccharomyces pombe, Torula* sp. and *Torulopsis* sp.

However, the gel glucans of the present invention may be derived from other suitable sources, e.g. bacterial, fungal or cereal glucans. The therapeutic activities of various glucans are well documented in the art and the processes of the present invention may be used to enhance activity of glucans in general, in particular in wound healing where the physical form and inter-molecular structure of the glucan product has been shown, by the present inventors, to be particularly significant. Without wishing to be bound by theory a rule of thumb is that the higher the weight average molar mass on a single chain basis of the glucan used according to the present invention, the more efficacious glucan gels may be produced.

The side chains of the glucan gels of the present invention usually comprise 2 or more β(1,3) linked glucosyl units. According to the present invention, single molecules linked to a main chain are not regarded as "side chains".

The glucans of the present invention preferably have side chains of, i.e. consisting or consisting essentially of, β(1,3) linked glucosyl units. In addition to the β(1,3) linked side chains, the glucans may also have one or more β(1,6) linked side chains. By altering the chains of the structure it is possible to alter the characteristics of the final product. There are many different ways of altering glucans including enzyme-treatment, use of acids like formic acid or hydrochloric acid or different bases as well as by other means. Preferred glucans are those which have been treated by acid (e.g. formic acid) or enzyme or any other suitable method to significantly reduce or eliminate the number of repetitive (1,6)-linked glucose molecules within the glucan. These (1,6)-linked glucosyl moieties would normally be found in the side chains of beta-glucans derived from yeast. The resulting glucans have β(1,3) main chains and β(1,3) side chains which are linked thereto through a single β(1,6) linkage which is not cleaved off by the elimination treatment.

The preferred glucans are essentially free of repetitive β(1,6) linked glucosyl residues. The single (1,6) linkages at the branch points (the β(1,3,6)-branching points) do not provide 'repetitive' β(1,6) linked glucosyl units. By 'essentially free' is meant less than 6%, preferably less than 4% and most preferably less than 3% of the total glucosyl units.

Some treatments, such as enzyme treatments, may leave up to 4 beta-1,6-linked, but typically 2 beta 1,6 linked glucosyl units uncleaved in the side chains. Such molecules are also 'essentially free' of repetitive beta 1,6-linked glucosyl units.

The distribution of linkages within preferred glucans of the invention may be represented as follows:

| Type of linked glucosyl residue | % |
|---|---|
| β(1,3) | 80-98 |
| β(1,6) | 0-6 |
| β(1,3,6) | 1-8 |
| Terminal | 0.01-6 |

β(1,3,6) refers to branch point residues which are (1,3) linked in the backbone and participate in a (1,6) connection to provide a side chain.

The glucan of the present invention could be in the form of a single, extracted fraction or two or more different fractions with different average molecular weights.

The glucans are underivatized in terms of chemical modifying groups.

The glucans of the invention are generated by a novel process. The inventors have found that treating an adequately concentrated solution of soluble glucan with an agent able to dissociate hydrogen bonds between glucan chains, followed by adding an agent able to restore interchain interactions, a novel gel glucan product is obtained with improved activity as compared to other similar glucan products. By doing this a highly randomly organized "haystack" gel will be created without having the typical triple helical structure of "annealed" beta-glucan chains. Surprisingly it was observed that this type of gel-structure was significantly more potent as immunomodulator than a classical organized soluble beta-glucan either in triple helical conformation or multiples of helixes.

Thus in a further aspect the present invention provides a method of producing a gel glucan product as defined above wherein an aqueous solution of glucan molecules is treated with an agent in order to dissociate hydrogen bonds between the glucan chains and then treated with an agent which enables the reformation of hydrogen bonds between the glucan chains.

Thus, the present invention provides a method of producing a glucan gel comprising the following steps:
  a) treating an aqueous solution of glucan molecules with an agent able to dissociate hydrogen bonds; and
  b) adding an agent rapidly able to reform hydrogen bonds.

Alternatively viewed the present invention provides a method of producing a gel glucan product as defined herein, said method comprising the following steps:
  a) treating an aqueous solution of glucan molecules with an agent which dissociates the glucan's hydrogen bonds; and
  b) contacting the product of step a) with an agent which enables reformation of hydrogen bonds within the glucan.

The dissociated and reformed hydrogen bonds may be intramolecular, i.e. within a single chain or intermolecular, between chains resulting in the formation of aggregates.

Preferably the agent able to dissociate hydrogen bonds is an alkali salt. Preferably the agent able to dissociate hydrogen bonds is used at a final concentration of above 50 mM, preferably about 150 mM.

Step a) is preferably performed at a temperature of 10° C. to 25° C., more preferably 15° C. to 20° C., most preferably about 18° C.

The addition of the agent able to dissociate hydrogen bonds is preferably performed slowly, preferably at a rate of approximately 1 liter per minute of 24 moles of NaOH dissolved in 10 liters of water, being added to 200 liters of 2% glucan solution or at an equivalent rate if the volumes or concentrations are different.

One such agent to dissolve hydrogen bonds between OH-groups in the poly-glucose chain would be sodium hydroxide (NaOH) in a sufficient concentration that would deprotonise the numerous OH-groups in the chains. This would lead to a complete dissociation of all intermolecular bonds typical for these high molecular weight glucans resulting in a random organization of the chains in solution. By neutralizing the solution by addition of acid to neutralize the alkali, the OH-groups are reformed and new hydrogen bonds between the chains can be established.

Using NaOH as the agent would typically need the addition of e.g. 2M NaOH solution to a final concentration of above 50 mM, or more preferably about 150 mM to a soluble glucan concentration of 1-6% in aqueous solution, more preferably 1.5-4% or most preferably 2-4%.

The step of reforming hydrogen bonds can also be viewed as neutralizing the solution following the addition of the agent able to dissociate hydrogen bonds.

Since the agent able to dissociate hydrogen bonds is preferably an alkali salt, then preferably the agent rapidly able to reform hydrogen bonds, i.e. the agent which neutralizes the solution produced in step a), is an acid, preferably a strong acid. Preferably the agents in step a) and step b) of the method are added in equimolar amounts. For instance, if 2M NaOH solution was added in step a) then in order to neutralize the solution an equimolar amount of e.g. 2M hydrochloric acid (HCl) can be added to the solution. Preferably the neutralization step is performed under agitation for a brief period which is long enough to ensure an efficient neutralization. For a volume of 1000 ml this step could be performed in less than 1 minute, e.g. less than 30 seconds. As shown in the Examples, larger volumes would necessarily take longer for all the acid to be added and mixed. After this the solution is left to establish the gel-conformation, for a volume of 1000 ml the time taken for gel formation may be 1 to 10 minutes, longer for larger volumes.

A rapid reformation of hydrogen bonds can be assessed in terms of the speed of gel formation. If a gel forms in less than 15 minutes from first addition of the agent (which can be considered a renaturing agent) then this is indicative of rapid reformation of hydrogen bonds, although "rapid" will typically mean less than 10 minutes, preferably less than 8 or 6 minutes, more preferably less than 4 minutes or 3 minutes. It being nonetheless appreciated that the larger volumes will generally necessitate longer time periods for gel formation/hydrogen bond reformation.

Any other agent having the ability to dissociate the hydrogen bonds could replace NaOH, and any other agent able to rapidly allow re-establishment of the hydrogen bonds forming a "haystack" type of gel could replace HCl. The skilled man is aware of other agents which can disrupt and then restore hydrogen bonds, bases and acids are particularly convenient as one can be readily balanced against the other to neutralize the impact of the agent which has disrupted hydrogen bonds. Other strong acids such as formic acid or sulphuric acid may be used. Also other alkali salts including, but not limited to, potassium hydroxide, lithium hydroxide, and calcium hydroxide, as well as possibly so called super-bases such as sodium hydride or sodium amide, can be potential agents for deprotonation and disruption of hydrogen bonds. Any acid with the appropriate quality can be utilized to neutralize the solution in order to restore hydrogen bonds—this includes, but not limited to, phosphoric acid, acetic acid, and citric acid. Urea or formamide are also commonly used to disrupt hydrogen bonds and could possibly be used in this process.

It will be appreciated that in a system involving large and complex organic molecules, it is not feasible or necessary to ensure that all hydrogen bonds have been disrupted or that all molecular chains participate in significant hydrogen bonding after conditions have been applied which enable the restoration of hydrogen bonding. However, the conditions applied will be such as to radically alter the organization and degree of hydrogen bonding in the glucan solution overall. The skilled reader is aware of the impact on a glucan solution of, for example, 150 mM NaOH and the concentration of other hydrogen bond breakers can be selected accordingly. The purpose of the second step, where conditions are provided which allow reestablishment of hydrogen bonds, is effectively to rapidly neutralise or reverse the effect on the potential for intermolecular electrostatic interactions caused by the addition of the hydrogen bond breaker. Thus the nature and concentration of this second agent will follow from the selection of the hydrogen bond breaker. It is also important to mention that the conditions of rapid neutralization provide for the "freezing" of an energetically metastable supermolecular structure which, without rapid neutralization would otherwise tend to re-organize in an energetically more optimal, but less bioactive manner. Further processes for increasing the stability of the final product resulting from the treatment according to the present invention, can of course be evaluated. Possible additional methods could be the addition of stabilizers or any method to establish a energetically more optimal molecular structure thus enhancing the stability of the final product without impairing its biological activity profile to a large degree.

In an industrial process the steps will conveniently be performed in a tank large enough to hold the entire batch of product.

The steps of hydrogen bond disruption and then restoration as described above may be repeated, e.g. once more.

Preferably, the method comprises a further step c) in which the ions (e.g. $Na^+$ and $Cl^-$) added during steps a and b above are removed, for instance via filtration. Methods of filtration are well-known in the art, for instance the product could be diafiltered over a tangential filter against the required volume of purified water.

The concentration of glucan in aqueous solution prior to the disruption of the hydrogen bonds is preferably 1.5-6%, more preferably 2 to 4%, most preferably about 2%. Preferably, the concentration of glucan in the glucan gel is about 2%, for instance 1.8% to 2.2%. Therefore, preferably the concentration of glucan in aqueous solution prior to the disruption of hydrogen bonds is also about 2%. The addition of agents in steps a) and b) of the above methods may increase the volume of the aqueous solution and so decrease the concentration of glucan in the solution. Preferably however the volume of agents added in steps a) and b) does not change the volume of the solution significantly, such that the concentration of glucan in the starting and end products is roughly equal. Of course, the skilled man will appreciate that, if desired, a higher concentration of glucan in the starting product can be used such that the addition of the agents in steps a) and b) leads to a precise, desired glucan concentration in the final product. The skilled man will be able to calculate the appropriate glucan concentration in the starting product and the appropriate volumes of agents to add in steps a) and b) to achieve a desired glucan concentration in the resulting gel product.

The above disruption and restoration of hydrogen bonding may be performed on any aqueous solution of glucan molecules; preferred glucans, including glucans with modified branching, are discussed above and the glucan solution will preferably be a yeast glucan solution. The starting material may be a gel, in which case step a) results in a non-gel solution and step b) reinduces a gelatinous state. The weight average molar mass ($M_w$) of the glucans in the starting solution is preferably high, preferably, on a single chain basis, the weight average molar mass of glucans in solution is above 15,000, more preferably above 20,000, most preferably above 25,000 g/mol. Suitable methods for determining these mass values are given above.

The methods of the present invention include methods in which a 1% to 4% aqueous solution of soluble beta-glucan is the starting material, to which is added NaOH at a concentration of about 2M to a final concentration of about 150 mM, the solution then being stirred until fully solubilised and clear. Gel form is re-established by adding an equimolar amount of HCl under stirring, which results in a gel with physiological osmolarity and pH of about 7. The gel can be produced in any volume.

The gels of the present invention can also be produced by a lay person when reagents, i.e. the starting material and the agents used in step a) and step b) are provided as a kit. Thus, in a further aspect the present invention provides a kit comprising a sealed vessel containing an aqueous solution of glucan molecules, a second sealed vessel containing an agent able to dissociate the glucan's hydrogen bonds and a third sealed vessel containing an agent able to reform hydrogen bonds within the glucan. The aqueous solution of glucan molecules, and the two agents comprising the kit may be as defined anywhere herein.

One such kit comprises a bottle of 85 ml 2.2% beta glucan in aqueous solution, a sealed tube of 7.5 ml 2M NaOH and a sealed tube of 7.5 ml 2M HCl, where the two latter reagents are added successively to the bottle of 2.2% beta glucan giving an isotonic 2% final gel. A further example is a kit comprising a bottle containing 70 ml 4% beta glucan in aqueous solution, a sealed tube of 15 ml 1M NaOH and a sealed tube of 15 ml 1M HCl, which results in 100 ml of a gel with concentration approximately (a little less than) 3% when the latter two reagents are added successively to the bottle of beta-glucan.

Glucans are generally extracted from their source material (e.g. fungi, yeast or cereal) in particulate form but methods of generating soluble forms from particulate glucans are known in the art and include acid or alkali treatments, such as the formolysis step described in WO 95/30022 and for instance various types of glucans from cereals like barley from Sigma Chemical. According to the present invention, a particulate starting material, such as may be prepared by the protocol in Example 1 of WO 95/30022, will preferably be solubilised by heating in formic acid for at least two hours. Formolysis performed on particulate glucan starting material may conveniently cause selective removal of any $\beta(1,6)$ linked glucosyl side chains as well as solubilising the particulate glucan.

The methods of the invention also optionally comprise a heating step where the formic acid treated product is boiled (>100° C.) for at least 30 mins. After the product has cooled it is preferably treated to remove particulate materials by regular methods know in the art e.g. by centrifugation or filtration.

The particulate glucan which is treated to yield a soluble form for processing in accordance with the present invention is preferably derived from cell walls, in particular yeast cell walls, which have had the protein components and other remnants like mannan and chitin removed therefrom e.g by washing.

One example of a suitable particulate yeast glucan product is produced by Biotec Pharmacon ASA which is derived from Bakers Yeast (*Saccharomyces cerevisiae*) and known as NBG COS®. Another example of particulate glucan raw materials are whole glucan particles like the product Imprime WGP™. The product is a natural underivatized (in terms of chemical modifying groups) particulate $\beta(1,3)/(1,6)$ glucan, characterised by NMR and chemical analysis to consist of polymers of beta-1,3-linked D-glucose containing side-chains of beta-1,3 and beta-1,6-linked D-glucose.

The visual appearance of preferred gel products of the present invention is firm, opaque, whitish with a high adhesion capacity to other surfaces.

In a further aspect the present invention provides a glucan product obtained or obtainable by any of the aforementioned processes.

The glucans of the present invention are potent therapeutic agents and in a further aspect the present invention provides the glucans as described herein for use in therapy, in particular for the treatment of conditions where a subject is in need of a systemic or local enhancement of the immune response, e.g. where there is tissue damage or infection. The glucans are of particular utility in assisting wound or ulcer healing and in the treatment of oral mucositis and cancer or reducing tumour size.

In a further aspect the present invention provides therefore a method of assisting wound or ulcer healing or treating oral mucositis in a subject in need thereof which comprises administration to said subject of a glucan of the present invention as described herein.

Reference is made to "assisting" wound or ulcer healing because some wounds or ulcers will heal naturally and others may not but the glucans of the invention have been shown to accelerate wound and ulcer healing. In some cases, healing may not occur satisfactorily without treatment. An example for such a wound which demands treatment for healing is diabetic foot ulcer. In this indication the patient develops wounds based on the underlying cause which is diabetes. Due to the often untreated underlying cause and the fact that these wounds are to be found on the feet of patients, these ulcers do not heal by themselves and cause huge problems for the patient usually ending in amputation of the foot.

In a further aspect the present invention provides a method of treating cancer or reducing the size of a tumour in a subject which comprises administration to said subject of a glucan of the present invention as described herein. Preferably the glucan is administered orally. Preferably, the glucan is administered at a dosage of 5 to 200 mg/kg/day, more preferably 20 to 100 mg/kg/day.

In a further aspect the present invention also provides a pharmaceutical composition comprising a glucan in gel form as defined above and one or more pharmaceutically acceptable diluents or carriers, preferably water and optionally one or more physiologically acceptable stabilisers or further diluents or carriers. The compositions may conveniently be formulated into any topical dosage form. The topical dosage forms may be gels, pastes, creams, sprays, lotions, solutions, ointments, films, etc.

In some variations, the compositions as described herein are in the form of an ointment. The ointment base may be an oleaginous base, an emulsifiable base, an emulsion base, or a water-soluble base. In other variations, the compositions according to the present invention are in the form of a cream. The creams may be viscous liquids or semisolid emulsions, either oil-in-water or water-in-oil. The cream bases may be water-washable, and contain an oil phase, an emulsifier, and an aqueous phase. In yet further variations, the compositions of the present invention are in the form of a lotion. The lotions may be formulated as suspensions of solids and contain suspending agents to produce better dispersions. The compositions according to the present invention may also be formulated pastes. Pastes are semisolid dosage forms in which the active agent is suspended in a suitable base. Depending on the nature of the base, pastes are divided between fatty pastes or those made from a single-phase aqueous gels.

In some variations, the compositions form a film on the wound surface. This film can be applied by a spray or other suitable means. To aid film formation, film forming agents such as, but not limited to, acrylic acid and its derivatives, polyacrylic and its derivatives such as polybutylmethacrylate and polymethacrylic acid, polymethacrylate, ascorbyl palmitate, carbomer, carnauba wax, cellulose derivatives such as cellulose acetate phthalates, rosca mellose sodium, hydroxyethyl cellulose, hydroxypropyl cellulose, hydroxypropyl methylcellulose, ethyl cellulose and related compounds, hydroxypropyl methylcellulose phthalate, hypromellose phthalate, cetyl alcohol and derivatives, microcystalline wax, poloxamer, polyethylene glycol, polyurethane, polyvinyl acetate, polyvinyl acetate phthalate, polyvinyl alcohol, silicone rubber and derivatives, shellac, triglycerides derivatives, and combinations thereof are used.

The compositions can also include at least one film plasticizer agent that may serve to soften the polymer film formed by the film forming agent so that it is sufficiently flexible to move with area of the body applied without cracking or peeling.

In some variations, the compositions may be cast into a film prior to application to the wound or applied to the wound directly where they polymerize in situ. A "spread-on" film polymerizes when applied to the skin and may be delivered as a cream or ointment from a tube, roll-on, spray, and the like. The film may be created by incorporating a silicone rubber, into the external phase. Upon mixing with the internal phase, the resultant emulsion is allowed to cure and provides a "spread-on" film, which polymerizes when applied to the wound. The emulsion may be spread onto a substrate to achieve a desired thickness.

In other instances, the compositions may be preformed into a layer or patch. The patch may be of varying thickness. The patch may also be cut to have a shape that generally follows the wound edges.

In some variations, the patches may include a pharmaceutically acceptable adhesive material that serves to affix the patch to the wound or skin. A patch backing layer may also be included.

The compositions may be directly placed on a wound, or placed on a substrate for application on a wound. Any substrate (carrier) may be used with compositions described here. For example, woven, non-woven, knitted, foam, and adhesive substrates may be used. Absorbent or non-absorbent substrates may also be used. In some variations, the compositions are sprinkled or spread on the substrate. In other variations, the compositions are impregnated within the substrate.

The wound dressings may be applied for any suitable time period. For example, they may be applied over a time period of one day, over several days, over several weeks, or for several months or more. In general, the wound dressings will be reapplied until the wound is healed. The duration of wound treatment with the dressings described here may depend on such factors as the type of wound being treated, wound location, wound exudates, and form of the composition being applied. Depending on the form used, the composition may be removed with water, or wiped or peeled off the wound.

The compositions described here may be used to treat wounds resulting from any etiology. For example, the wounds may be due to burns, infections, ischemia, lymphedema, neoplasms, neuropathy, radiation damage, surgical procedures, venous insufficiency, and trauma. The compositions of the present invention are of particular utility in assisting wound or ulcer healing.

The invention further provides a physical support, for example any medical device or material for medical use having applied thereto, including impregnated therein, a glucan of the invention as defined herein.

One important characteristic of such beta glucans is their water holding capacity and gel formation characteristics even in the absence of conditions like non-neutral pH or cations which might promote gel healing. Some beta-glucans would form gels at concentrations as low as 1%, but more typically in the range of 2-4%. A soluble beta-glucan from yeast like the one described herein will form a thixotropic and pseudoplastic gel when dissolved in aqueous solution at a concentration of 1-6% in pH range from 3-7, independent of the presence of cations.

The compositions of the invention comprise 1.5-6%, preferably 1.5-5% beta glucan in an aqueous solution, preferably the composition comprises around 2-3% glucan in an aqueous solution. The use of different concentrations is dependent on the purpose and the different modes of administration. As a general rule, a yeast glucan with a concentration of more than 6% in an aqueous solution and free from other stabilizing substances would result in a final gel product which is difficult to manufacture due to its solid gel properties.

Encompassed by the terms 'wound' and 'ulcer' are surface wounds, surgical wounds, burns, open fractures, leg ulcers, apthous ulcers, diabetic ulcers and decubitus ulcers. Wounds may be as a result of injury, surgery or disease but all are characterised by a loss of dermal integrity, the skin may be torn, cut or punctured and regrowth of the skin is required to seal the opening. The glucans of the present invention have been shown to accelerate wound closure. As shown in the Examples, efficacy can readily be demonstrated by measuring the size of an open wound.

The compositions are preferably applied topically, e.g. as a gel, transdermal patch, lotion, ointment, cream etc. Compositions may be applied daily, more frequently or less frequently, e.g. twice daily or on alternate days and for a duration as determined by a clinician or in some cases by the patient or other health advisor. The duration of treatment will depend on the nature and severity of the wound or ulcer with progress generally being readily determined by visual inspection.

Topical administration includes administration in the mouth and suitable gels, pastes, sprays, lozenges, etc. for delivery to the oral mucosa are known in the art.

The glucans and compositions containing them find utility in human and veterinary medicine. As used herein, the term 'medical' includes veterinary applications and contexts. Humans are preferred subjects for treatment but other animals which may usefully be treated include livestock and companion animals.

The glucans of the invention and compositions containing them may be applied to or incorporated in a physical/solid support such as a patch, dressing, plaster, bandage, film, gauze etc. which can be applied to the wound or ulcer site and such products constitute a further aspect of the present invention.

The glucans of the present invention also find corresponding utility in in vitro applications for the culturing of skin cell lines, e.g. for use in skin grafts. Thus in a further aspect the present invention provides an in vitro method of proliferation of skin cells which comprises contacting a population of skin cells with glucans of the invention as described herein.

It will be appreciated that preferred features applicable to one aspect or embodiment of the invention apply, mutatis mutandis, to all aspects and embodiments.

The glucans of the present invention have excellent in vivo efficacy as wound healing and anti-cancer agents, as shown in the Examples. The Examples also show the ability of the glucans of the invention to stimulate production of cytokines which are relevant in a variety of therapeutic contexts. The Examples show that the glucan of the present invention has different biological activity, as demonstrated by induction of cytokine production, as compared to a superficially similar glucan product which is also obtained from yeast, is soluble and has been treated to selectively reduce the (1,6) linked side chains while retaining (1,3) linked side chains. In particular, the glucan of the present invention can induce the differentiation of human myeloid dendritic cells towards an inflammatory phenotype, significantly stimulate TNF-alpha secretion and induce expression of G-CSF and IL-10 by these cells, while the secretion of CXCL-10 is basically at baseline level, and appears to be unaffected by the treatment described herein. This is important and illustrates that the preferred glucan of the present invention stimulates the secretion of a specific set or combination of cytokines. The glucan of the present invention can also stimulate macrophages from diabetic mice (db/db) to secrete CXCL2, PGE2 and GM-CSF, which all have prominent roles in wound healing. In addition, the gel glucans of the present invention activate the human complement system.

The effect of the preferred beta glucans on release of TNFα is dose-dependent and appears to diminish at glucan concentrations above a certain threshold value eg. 100 µg/ml in a variant of the RAW cell line overexpressing the beta glucan receptor dectin-1. Both the concentration yielding the maximal TNFα secretion, and also the magnitude of the response is higher compared to what is seen using a soluble beta glucan that has not been subjected to the treatment described herein.

The invention will now be further described in the following non-limiting Examples and the figures in which:

FIG. 1 shows storage modulus, G' (Pa), plotted against temperature for a glucan gel according to the present invention. The data was obtained by small strain oscillatory measurements using a Stresstech HR rheometer and the following temperature scan: 70 to 10° C. at a rate of ⅓° C./min, kept at 10° C. for 2 h and then 10 to 70° C. at a rate of ⅓° C./min. The melting temperature of this gel (gel to sol) is determined to approximately 40° C. based on where the increasing temperature curve levels out (G'≈0 Pa).

Figure 11A:
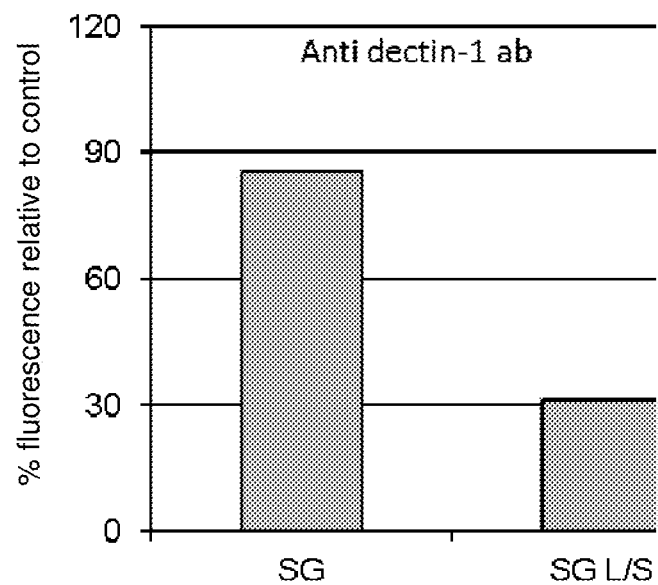
Figure 11B:
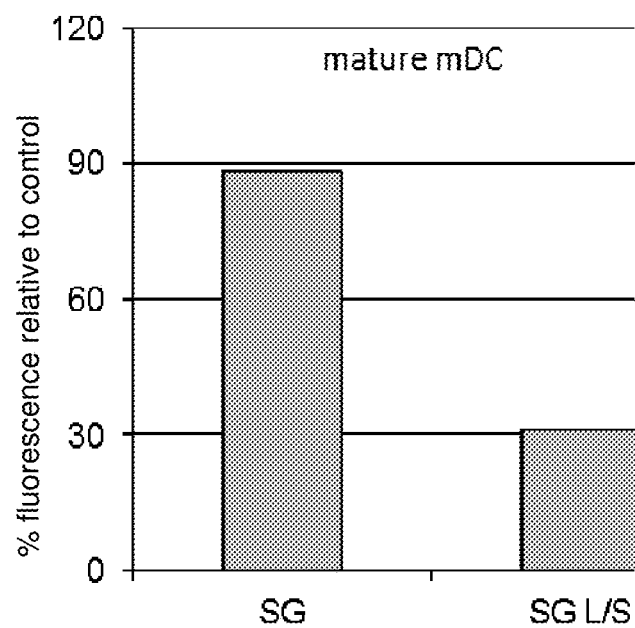

FIGS. 11A and 11B show fluorescence in human in-vitro differentiated, blood monocyte derived, myeloid dendritic cells feed DTAF-stained SG (100 µg/ml) and SG-LS (20 µg/ml) for 2 h. DTAF was detected by FACS. Level of DTAF was studied in immature cells pretreated by a dectin-1 binding antibody (antagonist) (11A), or mature mDC (11B). The DTAF level in glucan-feed immature cells pretreated with PBS alone (a, b), served as controls (100%). Y-axis denotes percentage fluorescence compared to controls.

Figure 12A:
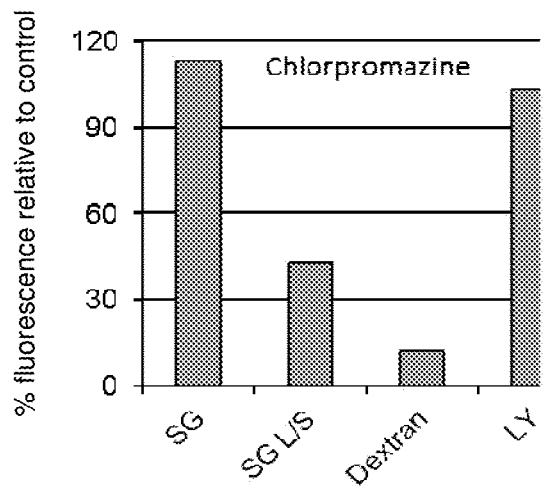
Figure 12B:
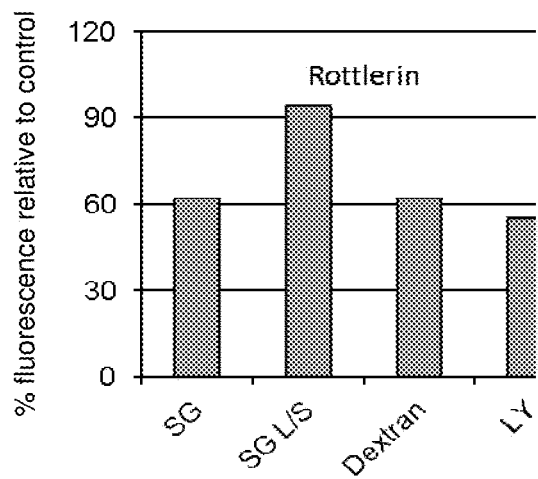
Figure 12C:
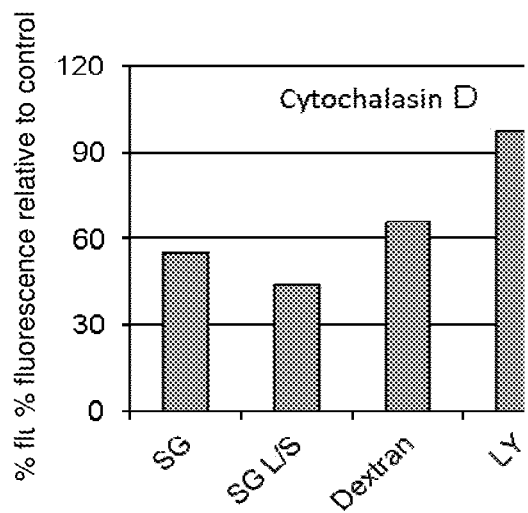

FIGS. 12A-12C show fluorescence in human in-vitro differentiated, blood monocyte derived, myeloid dendritic cells feed DTAF-stained SG (100 µg/ml), SG-LS (20 µg/ml), dextran and luciferase yellow (LY) for 2 h. Dextran is a clathrin-dependent control ligand, while LY is a fluid-phase (macropinocytosis) marker. DTAF was detected by FACS. Level of DTAF was studied in immature cells pretreated by the indicated inhibitors. FIG. 12A shows DTAF levels in the presence of the inhibitor Chlorpromazine, FIG. 12B shows DTAF levels in the presence of the inhibitor Rottlerin, and FIG. 12C shows DTAF levels in the presence of the inhibitor Cytochalasin D. The DTAF level in glucan-feed immature cells pretreated with PBS alone served as controls (100%). Y-axis denotes percentage fluorescence compared to controls.

EXAMPLES

Example 1

Preparation of Gel Glucan Product of the Present Invention (SG-LS)

An aqueous solution of 2% yeast glucan molecules was treated as described below. This aqueous solution was prepared from a particulate glucan preparation by formolysis to selectively remove β-1,6 side chains and subsequent purification and diafiltration to remove particulate matter and low molecular weight components from the formolysis solution. A suitable formolysis step is disclosed in Example 3 of EP 0759089 B1. The particulate glucan was itself prepared from cell walls of Baker's Yeast (*S. cerevisiae*) by separate extractions with alkali, ethanol and water, each extraction being followed by appropriate drying (spray drying and vacuum drying).

a. Disruption of Hydrogen Bonds by Addition of Sodium Hydroxide:

Addition of sodium hydroxide took place after the concentration of the glucan solution had been adjusted, giving a product volume of approximately 200 liters in a closed and agitated 800 liter tank which is heated or cooled by introduction of steam or water to a jacket surrounding the tank.

The product temperature was adjusted to 18° C., and 24 moles of NaOH, dissolved in approximately 10 liters of purified water, was poured slowly (approximately 1 liter per minute) through a hatch in the tank.

b. Restoration of Hydrogen Bonds by Addition of Hydrochloric Acid:

The restoration process was started immediately after the last of the NaOH has been poured into the tank.

Slightly less than 24 moles of HCl, approximately 9 liters of a 2.4M solution in purified water, was poured into the tank relatively quickly (in approximately 2 minutes), the pH of the product was measured, and more acid added in small portions until pH reached approximately 4.

c. Removal of Salt

To remove the ions ($Na^+$ and $Cl^-$) added during steps a and b, the product can be diafiltered over a tangential filter against the required volume of purified water.

Example 2

Stimulation of Human Dendritic Cell Maturation

The potency of different formulations of soluble beta-glucan to differentiate monocyte derived immature dendritic cells (iDC) into mature dendritic cells (mDC) differs. The level of activation can be visualised by measuring the expression of selected DC cell surface markers.

Human monocytes purified by lymphoprep gradient followed by magnetic cell sorting (MACS) with anti-CD14 microbeads were cultured for 5 days with a combination of IL-4 and recombinant human GM-CSF to promote the differentiation into immature dendritic cells. The monocyte derived immature dendritic cells (iDC) were cultivated at $physO_2$ levels. From day 5 to day 6 the iDC were stimulated with 50 µg/ml soluble beta-glucan (SG), or 10 ug/ml non-soluble beta glucan (NG).

Expression of the surface molecules HLA-DR, CD83 and CD86 were used to survey the differentiation of iDC into mature DC, and were analyzed by fluorescent activated cell sorting FACS. Also expression of C-type lectin receptor DC-SIGN was analysed.

Compared to the negative control (PBS) soluble glucan (SG), which is the post-formolysis, pre-NaOH treated glucan of Example 1 and is a glucan present in aqueous solution at a concentration of 2%, slightly downregulates the expression of CD83, CD86, MHC class II (HLA DR) and DC-SIGN. The down regulation is primarily a result of a lover number of cells expressing the protein, while expression of the CD86 protein is slightly down regulated per cell as well. In contrast, SG-LS, a glucan according to the present invention and prepared in accordance with Example 1, is a powerful stimulus which activates iDCs to upregulate the expression of CD83, CD86, and HLA-DR. Also in contrast to SG the expression of DC-SIGN is efficiently down regulated by SG-LS. Non-soluble beta glucan from *Saccharomyces cerevisiae* activates a similar pattern of protein expression of CD83, CD86, HLA-DR and DC-SIGN as SG-LS, although even more powerful. Down regulation of DC-SIGN in conjunction with up regulation of CD83, CD86 and MHC class II are accepted hallmarks of dendritic cell activation. Thus, SG-LS activates dendritic cells in vitro, while SG does not, and that the properties of SG-LS with respect to this function resembles non-soluble beta glucan particles from *S. cerevisiae*.

Example 3

Stimulation of Cytokine Secretion by Human Dendritic Cells (DCs)

To determine the cytokine profile secreted by human DCs in vitro, peripheral blood monocytes were isolated and propagated into mDC using standard methods. The mDCs were subsequently stimulated with different concentrations of soluble beta-glucans, either alone or in concert with bacterial lipopolysaccharide (LPS) (1 $ngml^{-1}$). The cytokine profile was determined by multiplex analysis using the Luminex system. FIG. 2 shows that SG stimulation leads to a weak induction of TNFα secretion, whereas G-CSF, IL-10, CXCL-10 and IL-12 remain unaffected. In contrast, SG-LS ("421-4 new" in FIG. 2) strongly stimulates TNFα secretion as well as a low level secretion of both G-CSF and IL-10.

SG is not a glucan in accordance with the invention, but can be potentiated according to the presented protocol as illustrated by SG-LS, which is a gel glucan product in accordance with the present invention and prepared in accordance with Example 1.

The secretion of CXCL-10 was, as for SG, not affected by SG-LS stimulation, while the production of IL-12 was weakly inhibited by SG-LS.

Costimulation of human mDCs with SG or SG-LS together with LPS revealed that SG-LS has a synergistic or additive effect on the secretion of TNFα, CXCL-10, IL-10, and G-CSF, while secreation of IL-12 was clearly downregulated compared to LPS alone (FIG. 3). Costimulation of SG and LPS did not induce any clear changes in any of the cytokines tested (FIG. 3).

Taken together, SG and SG-LS induce distinctive biological functions from in vitro stimulated human mDC.

The example shows that the soluble glucan produced according to the present invention has a stronger ability to modulate the effect of other pathogen associated molecular patterns as compared to a soluble glucan not subjected to the procedure described herein.

Example 4

Stimulation of Cytokine Secretion by Mouse Macrophages

Macrophages from diabetic (db/db) mice (BKS.Cg-m $Dock7^m$+/+$Lepr^{db}$/J) were harvested by intraperitoneal lavage using PBS supplemented by EDTA. The cells were seeded in microplates and stimulated with either SG or SG-LS for 12 h at 37° C., either alone or in combination with LPS. The supernatant was analyzed by ELISA for a series of signaling molecules involved in wound healing and inflammation.

Figure 4:
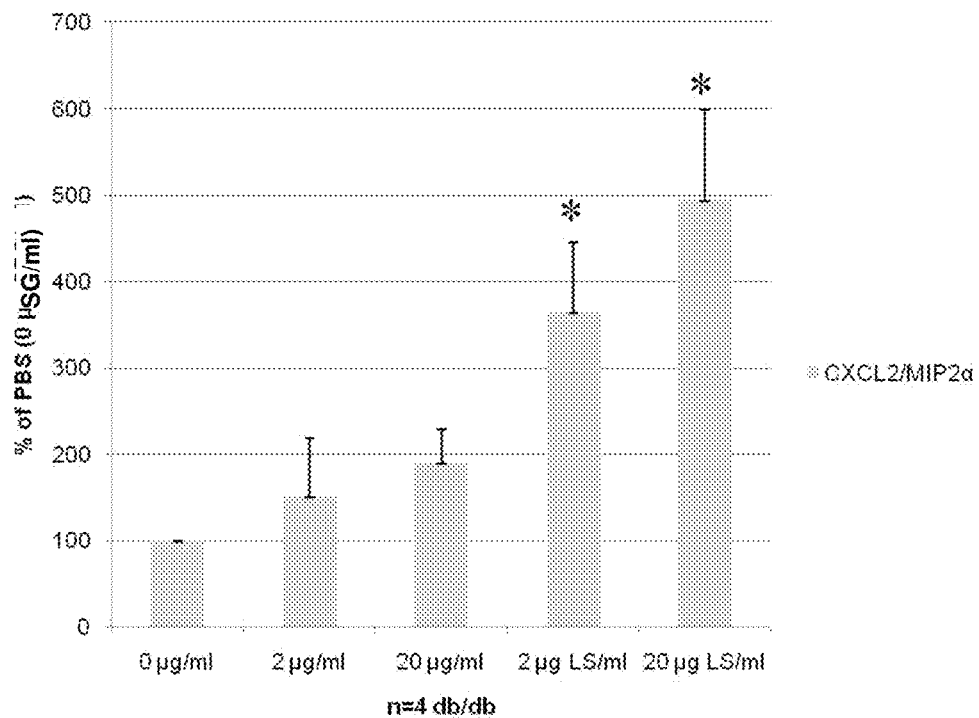
FIG. 4 shows secretion of CXCL2 by macrophages from db/db mice stimulated by different concentrations SG and SG-LS. LS denote SG-LS. *p<0.05.

Both SG and SG-LS stimulated macrophages from the db/db mouse to secrete CXCL2 (FIG. 4). The concentration of the secreted chemokine in the supernatant from the SG stimulated cells were not significantly different from the what was measured from cells given phosphate buffered saline only. In contrast, cells given SG-LS secreted significantly more CXCL2 than the control cells.

Figure 5:
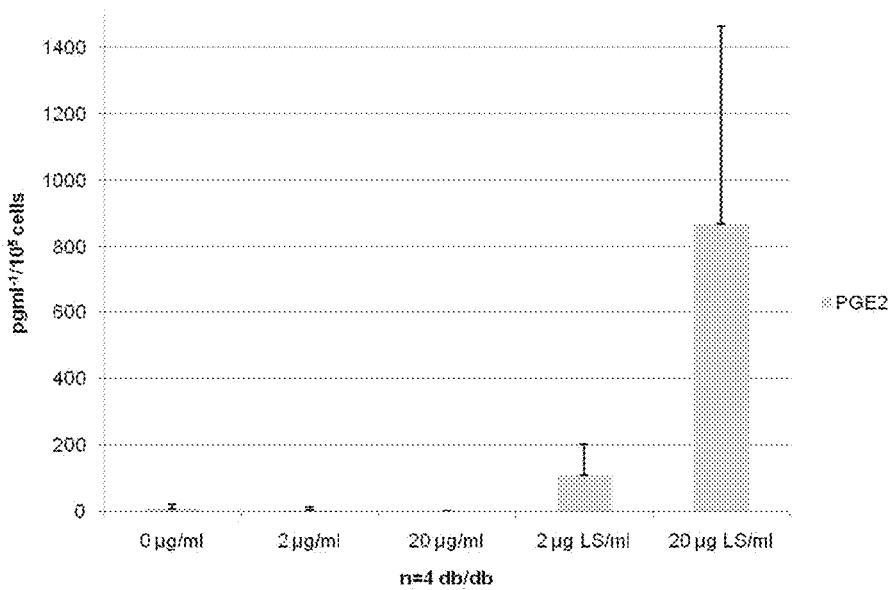
FIG. 5 shows secretion of PGE2 by macrophages from db/db mice stimulated by different concentrations of SG and SG-LS. LS denote SG-LS.
Figure 6:
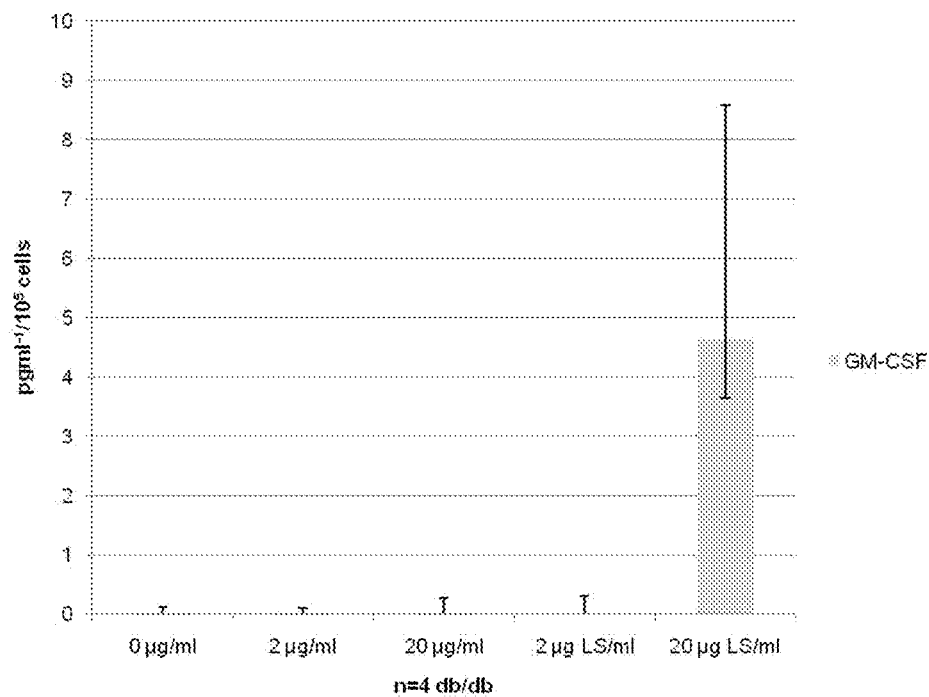
FIG. 6 shows secretion of GM-CSF by macrophages from db/db mice stimulated by different concentrations SG and SG-LS. LS denote SG-LS.

Macrophages from db/db mice stimulate by SG-LS secrete PGE2 (FIG. 5) and GM-CSF (FIG. 6). Due to a high variation in the assay the concentrations in the supernatants of either signaling molecule were not significantly different from the concentrations in the supernatants from cells incubated in phosphate buffered saline. On the other hand, SG did not stimulate secretion of either PGE2 or GM-CSF (FIGS. 5 and 6, respectively).

Example 5

Stimulation of TNFα Secretion by RAW/Dectin-1 Cell Line

The RAW/dectin-1 cell line is a stable transfectant of the RAW264.7 mouse leukaemic monocyte macrophage cell line over-expressing the beta-glucan receptor, dectin-1. The cell line corresponds to the RAW blue™ cell line from Invivogen. The cell line is suitable to determine individual differences between different formulations of soluble beta glucan, and the beta glucan response mounted by this cell line is indicative of an interaction with the dectin-1 receptor.

Figure 7:
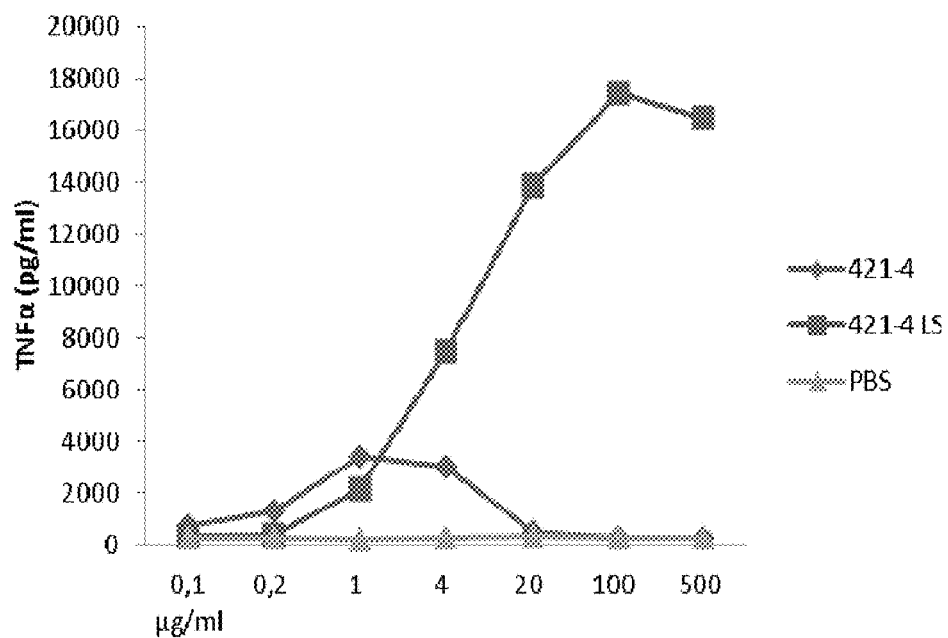
FIG. 7 shows the secretion of TNFα by a dectin-1 over-expressing RAW cell line stimulated by either SG (421-4), SG-LS (421-4 LS). Phospahate buffered saline served as a negative control.

Both SG and SG-LS induce secretion of TNFα as measured in an ELISA based assay 24 h after stimulation at 37° C. (FIG. 7). Both formulations induce a typical dose-response. The maximal effect of SG is approached by 1-2 µg/ml, and declines at lower or higher concentrations. In comparison the maximal effect of SG-LS is seen at 100 µg/ml giving rise to a 5-fold higher concentration of TNFα in the medium surrounding the cells.

Thus, both SG and SG-LS stimulates a dectin-1 over-expressing murine cell line to secrete TNFα, but the responses are characteristic and easily distinguishable. While the response to SG diminish above 4 µg/ml, the response to SG-LS becomes stronger until 100 µg/ml. This suggests that SG and SG-LS interacts differently to the major beta glucan receptor, dectin-1.

Example 6

Wound Healing In Vitro

The impact of SG and SG-LS, respectively, on wound healing was investigated by analysing the repair of full-thickness excisional skin wounds in the diabetic (db/db) mouse model (i.e. BKS.Cg-m Dock7$^m$+/+Lepr$^{db}$/J mice). Upon acclimatisation (5-7 days without disturbance) the animals were housed in groups of 5 animals according to Home Office regulations and the specific requirements of diabetic animals. After experimental wounding, animals were housed in individual cages (cage dimensions 35×15× 15 cm with sawdust bedding, changed twice weekly), in an environment maintained at an ambient temperature of 23° C. with 12-hour light/dark cycles. The mice were provided with food (Standard Rodent Diet) and water ad libitum. Following all anaesthetic events, animals were placed in a warm environment and monitored until they were fully recovered from the procedure. All animals received appropriate analgesia (buprenorphine) after surgery and additional analgesics as required. All animal procedures were carried out in a Home Office licensed establishment under Home Office Licences (PCD: 50/2505; PPL: 40/3300; PIL: 50/3482; PIL: 70/4934). The health of animals was ill monitored on a daily basis throughout the study.

On day 0, animals were anaesthetised (isofluorane & air) and the dorsum shaved and cleaned with saline-soaked gauze. A single standardised full-thickness wound (10.0 mm×10.0 mm) was created in the left dorsal flank skin of each experimental animal. Wounds in all treatment groups were subsequently dressed with a circumferential band of the transparent film dressing Bioclusive™ (Systagenix Wound Management, UK); after which they received either SG or SG-LS by injection 50 µl of a 2% solution in purified water through the Bioclusive film using a 29-gauge needle. Diabetic animals were randomized to one of the treatment regimes using appropriate software. For the experimental groups receiving either SG or SG-LS treatments was reapplied on post-wounding days 2, 4 and 6. Wound sites in these animals were closely monitored for excessive build-up of applied agents and excessive wound site hydration; if excessive applied agent accumulation/hydration was apparent, previously applied material was removed by aspiration prior to reapplication. For the positive control group treatments was reapplied daily until post-wounding day 6—wounds in this group received a total of 7 applications of the growth factor combination treatment. On post-wounding days 4, 8 and 12 all animals were re-anaesthetised, their film dressings and any free debris removed, and their wounds cleaned using saline-soaked sterile gauze. After photography on days 4 and 8, wounds were re-dressed as above with Bioclusive film dressing.

Figure 8:
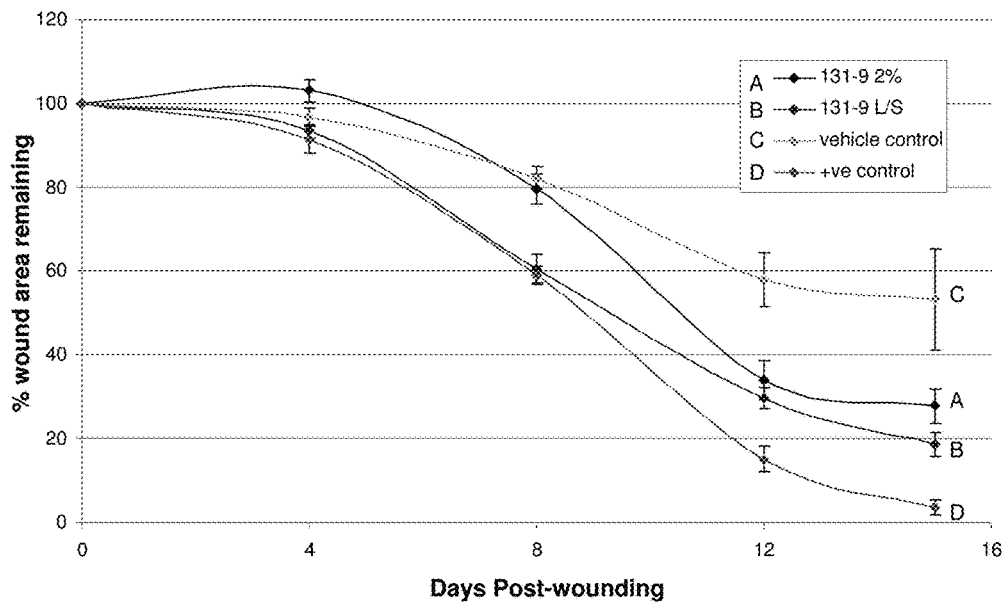
FIG. 8 shows SG 131-9 2% and potentiated (L/S) 131-9 2% versus vehicle (water) and positive control (rh-PDGF-BB (10 µg)+rh-TGF-α (1 µg) in 0.5% HPMC), mean±s.e.m. *p<0.05. **p<0.01.
Figure 9:
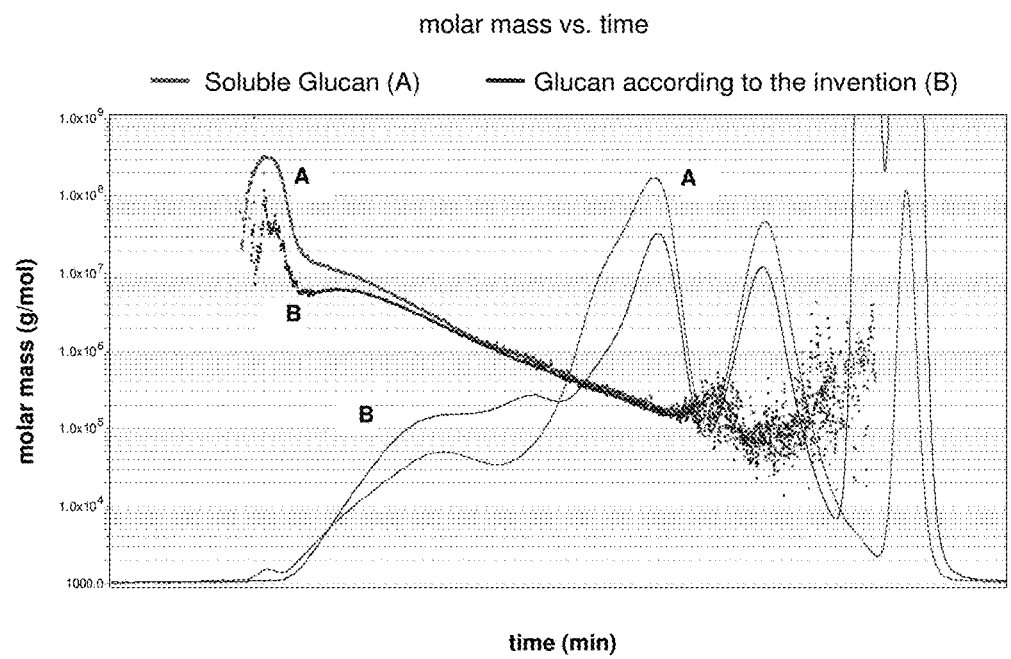
FIG. 9 shows SEC-MALS-RI chromatograms in aqueous solution of a potentiated glucan produced according to the present invention together with the starting glucan prior to treatment with alkali and acid. The profiles are similar, but it is apparent that very high molecular weight aggregates have been removed by the procedure.

Wound closure data were determined from scaled wound images taken of each wound at each assessment point. The area of a given wound, at a given time point, was expressed as a percentage of the area of that wound immediately after injury (i.e. day 0). The mean percentage wound area remaining (& standard error of mean) was calculated for each group and was displayed graphically (FIG. 8). The impact of each glucan preparation was compared to that of wounds in receipt of: i). vehicle (water); and ii) PDGF-BB+TGF-α (positive control).

Wounds in receipt of SG 131-9 LS 2% displayed elevated wound closure, relative to wounds in receipt of SG 131-9 2%, at all time points assessed (FIG. 8). This observed difference was statistically significant at days 4 and 8 ($p=0.015$ & $0.001$ respectively). At the early time points (days 4 and 8) the wound closure profile of the SG 131-9 LS treated wounds was comparable to that of positive control treated-wounds.

Example 7

Determination of Melting Point

Figure 1:
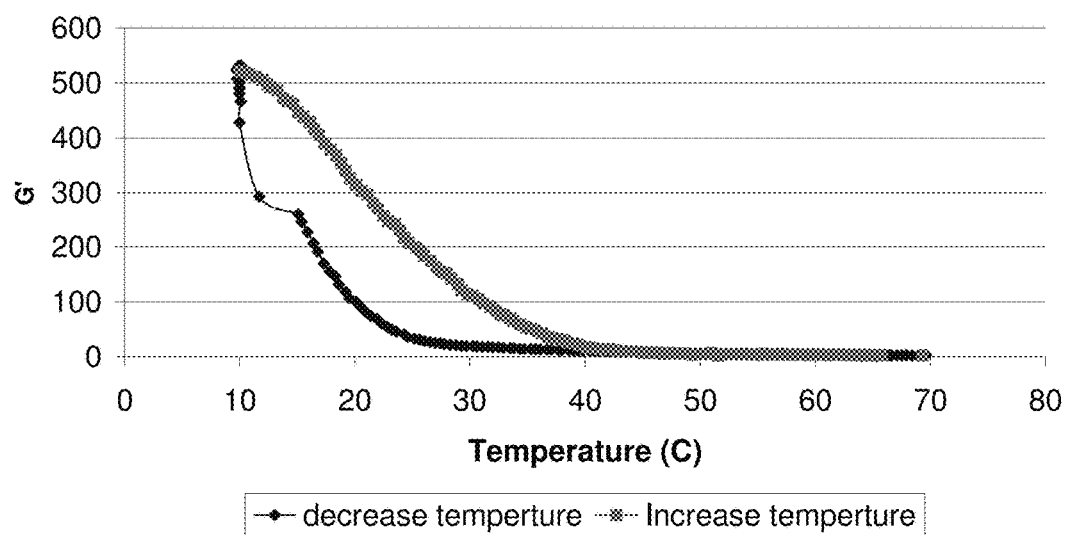
Figure 2A:
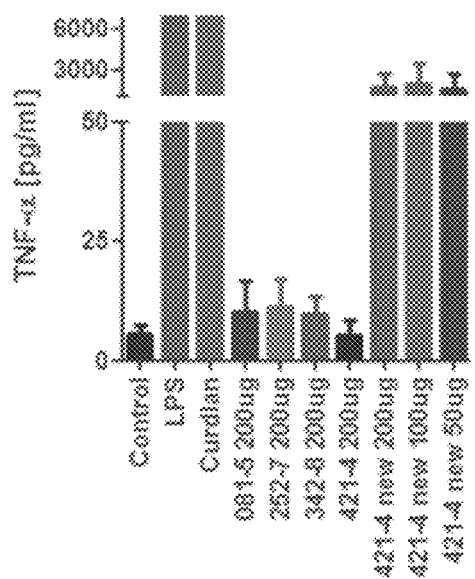
FIGS. 2A-2E show in vitro stimulation of human mDC with different batches and concentrations of SG (081-5, 252-7, 342-8, 421-4) and different concentrations of SG-LS (421-4 new). The concentration of secreted 2A) TNFα, 2B) G-CSF, 2C) IL-10, 2D) CXCL-10 and 2E) IL-12p70 are indicated along the y-axis.
Figure 2B:
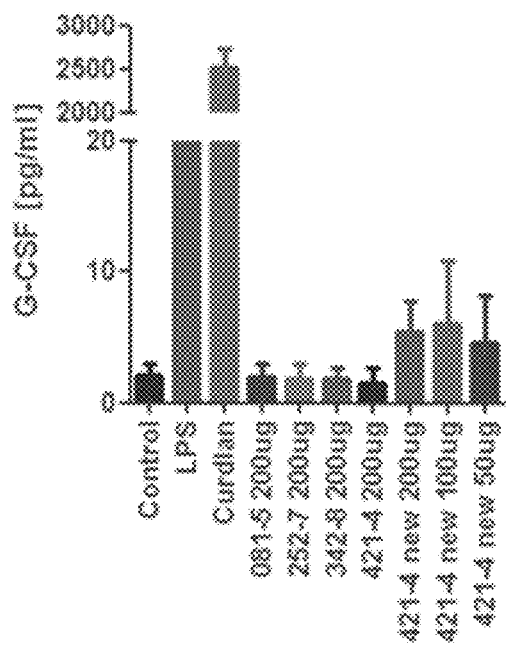
Figure 2C:
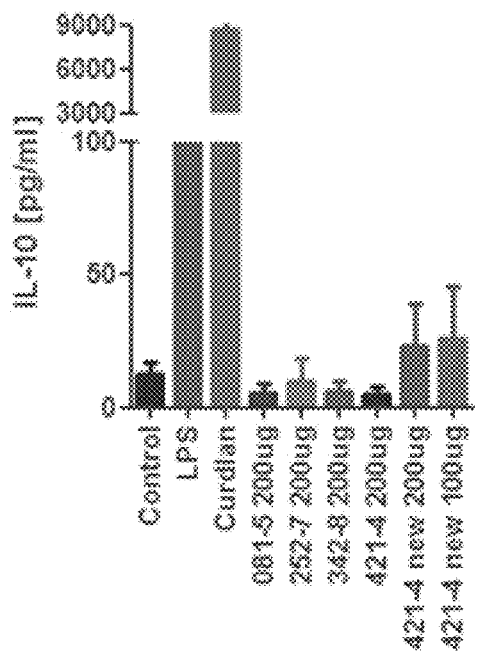
Figure 2D:
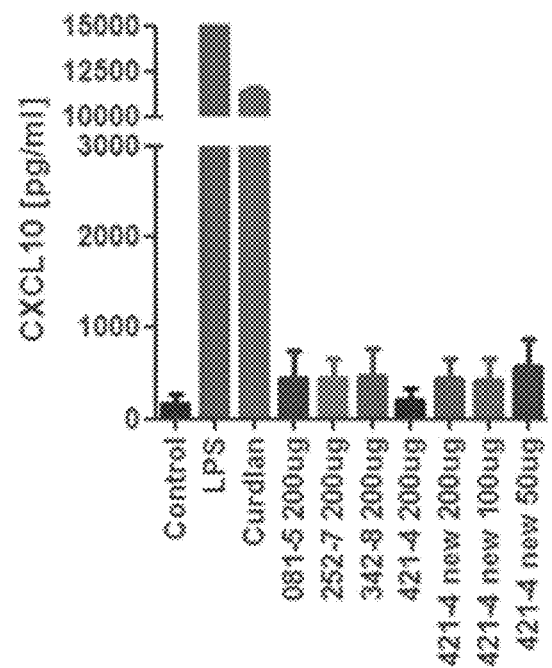
Figure 2E:
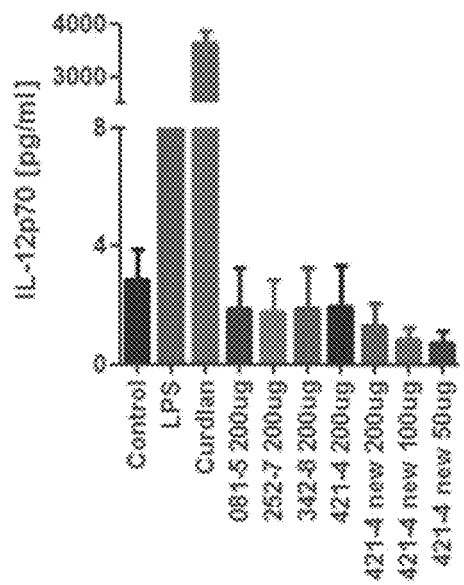
Figure 3A:
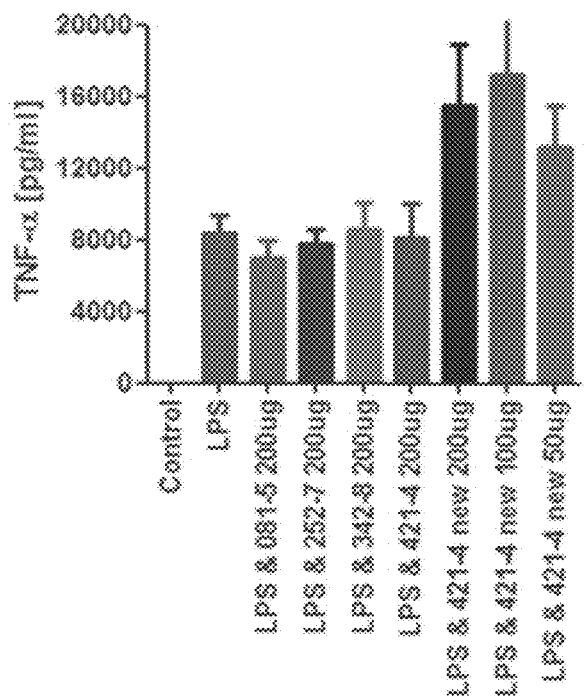
FIGS. 3A-3E show in vitro costimulation of human mDC with LPS in and different batches and concentrations of SG (081-5, 252-7, 342-8, 421-4) and different concentrations of SG-LS (421-4 new). The concentration of secreted 3A) TNFα, 3B) G-CSF, 3C) IL-10, 3D) CXCL-10 and 3E) IL-12p70 are indicated along the y-axis.
Figure 3B:
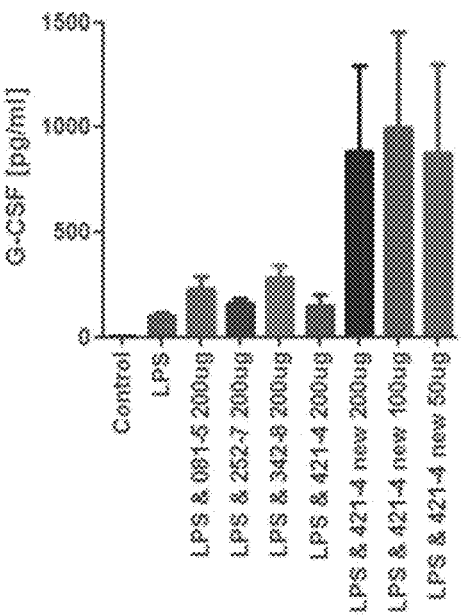
Figure 3C:
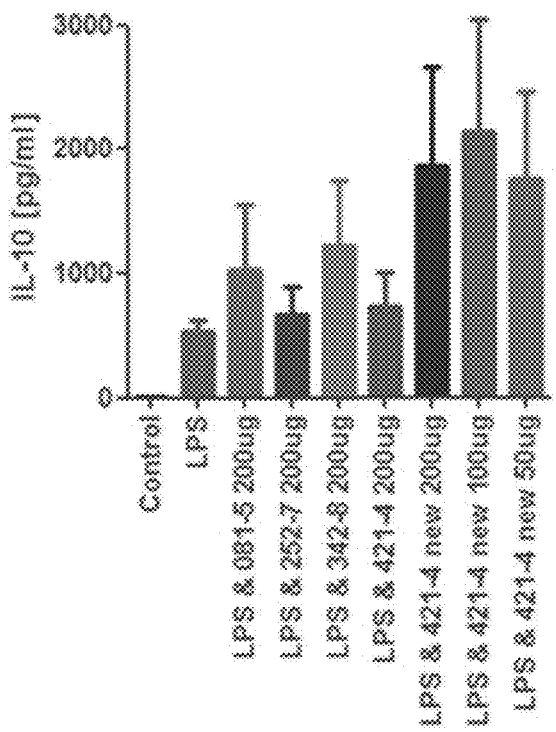
Figure 3D:
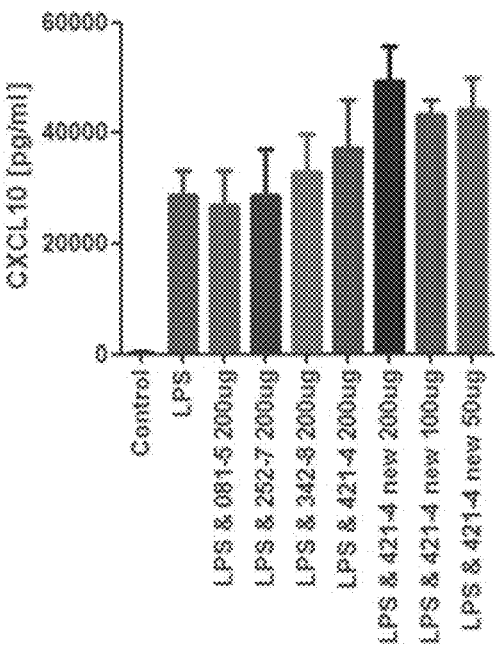
Figure 3E:
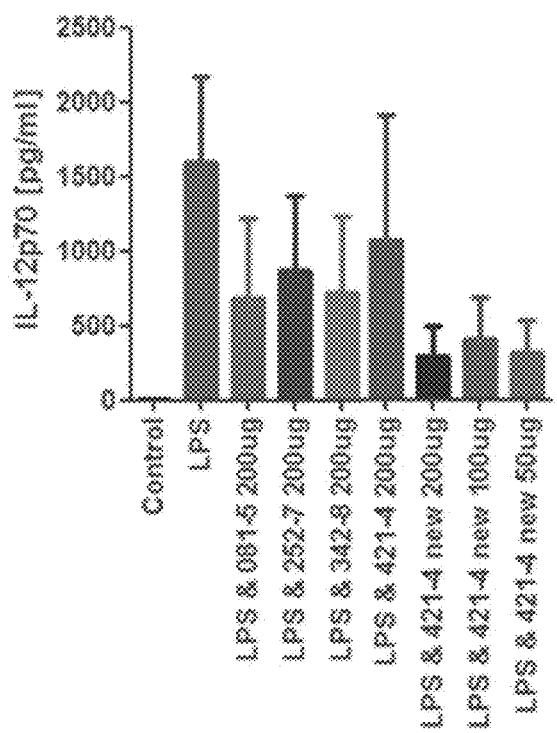

Determination of the melting point of a glucan gel produced according to the present invention was performed as described in the description and the results are shown in FIG. 1. The alkali-acid treatment generally increases the melting temperature (gel to sol) of the glucan gel.

Example 8

Figure 10:
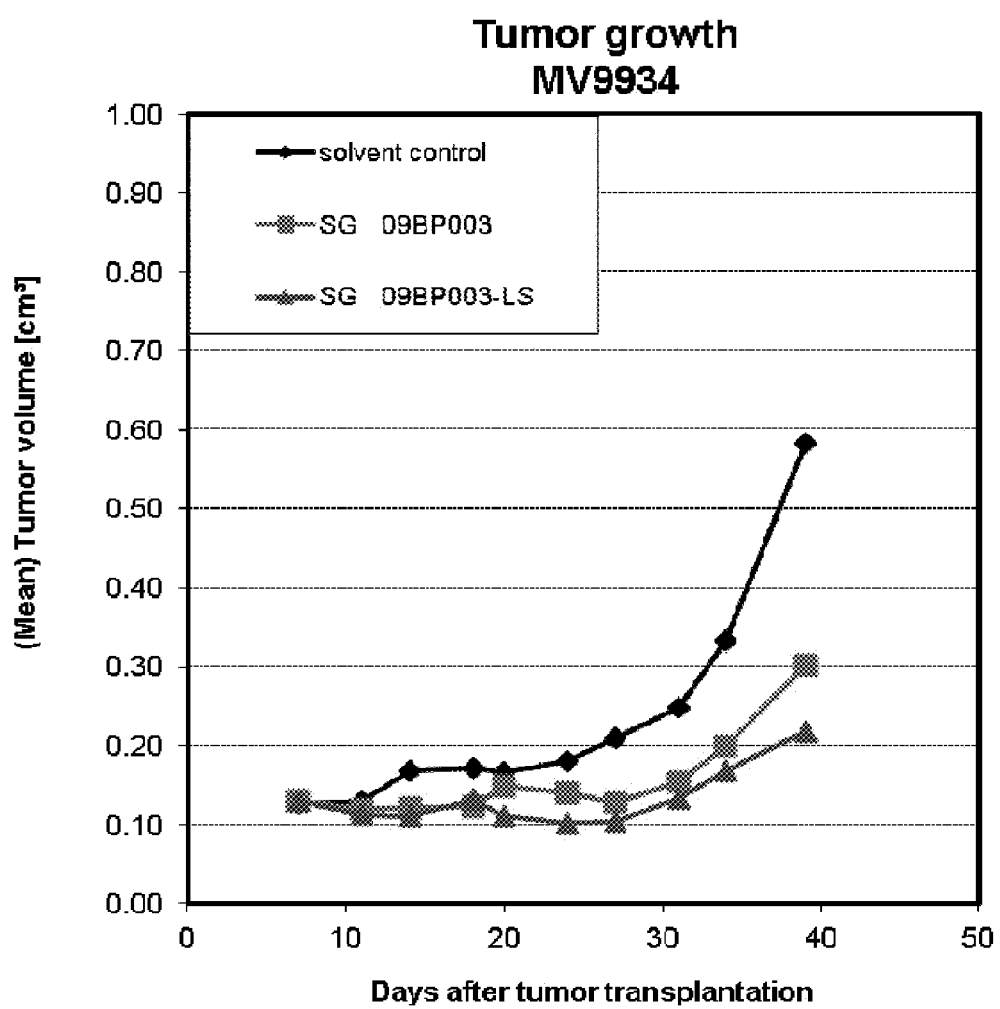
FIG. 10 shows growth of xenogeneic BT474 tumor cells transplanted intradermally into nude mice. SG (09BP003), SG-LS (09BP003) or water (solvent control) was given p.o. every second day from day 7 until day 38.

The impact of SG and SG-LS, respectively, on anti-tumour activity was investigated using NMRI nu/nu mice with an intradermal transplant of $10^7$ BT474 cells in matrigel. After a period of tumour growth, 7 days until palpable (80 mm$^3$), SG and SG-LS were administered daily by oral cavage. Tumour diameter was measured every second day over a 31-day period, and volumes determined. The analysis (FIG. 10) revealed that both SG and SG-LS delayed tumour growth compared to the vehicle (water). It was also clear that SG-LS inhibited the growth rate more efficiently than compared to SG, suggesting that also the anti-cancer properties of SG are potentiated by the herein described method of production.

Example 9

The difference in efficacy between SG and SG-LS was investigated by analysing their mechanisms of cellular interaction and the results are shown in FIGS. 11 and 12. Uptake of the LS variant in human in-vitro generated myeloid dendritic cells derived from blood monocytes (mDC) is inhibited by a dectin-1 antagonist (anti-dectin-1 antibody, FIG. 11 a). Uptake of SG was only slightly inhibited by the antibody suggesting that SG enters the cell primarily by mechanism independent of dectin-1. This finding was further substantiated by studying the uptake of fluorescein-labeled glucans in mature mDC and immature mDC. It is well known that the surface expression of dectin-1 is lower in mature relative to immature mDC, and hence uptake of SG-LS in mature mDC is reduced (~30%, FIG. 11b)) compared to immature mDC (100%, not shown). The uptake of SG was similar in both mature and immature mDC, supporting the dectin-1-antagonist data, and suggesting that SG-LS and SG interacts differently with the cells.

The precise mechanisms were determined using specific inhibitors (FIG. 12). Uptake of SG was unaffected by chlorpromazine, while endocytosis of SG-LS was inhibited by this compound. This suggests that SG-LS is taken up by clathrin-mediated endocytosis, while SG is not. On the other hand, uptake of SG is inhibited by rottlerin which interferes with macropinocytosis. Intracellular accumulation of SG-LS is not affected by rottlerin. Cytochalasin D partially inhibits the uptake of both ligands, suggesting a requirement for cytoskeleton rearrangements, i.e. phagocytosis, to enter the cells. Taken together these results demonstrate that SG and SG-LS are taken up by a different mechanisms, although phagosytosis is common to both.

The invention claimed is:

1. A method of assisting wound or ulcer healing or treating oral mucositis or cancer in a subject in need thereof which comprises administering to said subject a gel glucan product comprising a soluble yeast glucan in aqueous solution at a concentration of 1 to 6%, the glucan having a weight average molar mass of 15,000 to 50,000 g/mol on a single chain basis and a weight average molar mass in aqueous solution on an aggregate basis of 4 to $20\times10^5$ g/mol, the gel glucan product having a gel to sol melting temperature of 35 to 60° C.

2. The method of claim 1, wherein the glucan has a weight average molar mass of 20,000 to 40,000 g/mol on a single chain basis.

3. The method of claim 1, wherein the gel glucan product has a melting temperature (gel to sol) of about 40° C.

4. The method of claim 1, wherein the glucan is in aqueous solution at a concentration of 2% to 4%.

5. The method of claim 1, wherein the glucan is in aqueous solution at a concentration of about 2%.

6. The method of claim 1, wherein the glucan is derived from *Saccharomyces cerevisiae*.

7. The method of claim 1, wherein the glucan is a beta glucan comprising a backbone of β-(1,3)-linked glucosyl residues and side chains comprising 2 or more β-(1,3)-linked glucosyl residues, the sidechains being attached to the backbone via a β-(1,6)-linkage.

8. The method of claim 1, wherein the glucan is essentially free of repetitive β-(1,6)-linked glucosyl residues.

9. The method of claim 1, wherein said ulcer is a diabetic ulcer.

10. The method of claim 1, wherein the glucan is topically applied to a subject.

11. A physical support having applied thereto or impregnated therein, a gel glucan product comprising a soluble yeast glucan in aqueous solution at a concentration of 1 to 6%, the glucan having a weight average molar mass of 15,000 to 50,000 g/mol on a single chain basis and a weight average molar mass in aqueous solution on an aggregate basis of 4 to $20\times10^5$ g/mol, the gel glucan product having a gel to sol melting temperature of 35 to 60° C.

12. The physical support of claim 11 selected from the group consisting of a woven, non-woven, knitted, foam or adhesive substrate; a patch, dressing, plaster, bandage, film or gauze.

13. An in vitro method of proliferation of skin cells which comprises contacting a population of skin cells with a gel glucan product comprising a soluble yeast glucan in aqueous solution at a concentration of 1 to 6%, the glucan having a weight average molar mass of 15,000 to 50,000 g/mol on a single chain basis and a weight average molar mass in aqueous solution on an aggregate basis of 4 to $20\times10^5$ g/mol, the gel glucan product having a gel to sol melting temperature of 35 to 60° C.

* * * * *